(12) United States Patent
Giri et al.

(10) Patent No.: US 9,662,017 B2
(45) Date of Patent: May 30, 2017

(54) METHODS AND SYSTEMS FOR ACQUIRING MULTIPLE INTERLEAVED SLICES IN MAGNETIC RESONANCE IMAGING

(71) Applicants: Siemens Aktiengesellschaft, München (DE); NorthShore University HealthSystem Research Institute, Evanston, IL (US)

(72) Inventors: Shivraman Giri, Chicago, IL (US); Robert R. Edelman, Highland Park, IL (US); Xiaoguang Lu, West Windsor, NJ (US); Carmel Hayes, München (DE)

(73) Assignees: Siemens Healthcare GmbH, Erlangen (DE); Northshore University Healthsystem, Evanston, IL (US)

( * ) Notice: Subject to any disclaimer, the term of this patent is extended or adjusted under 35 U.S.C. 154(b) by 607 days.

(21) Appl. No.: 14/242,924

(22) Filed: Apr. 2, 2014

(65) Prior Publication Data

US 2015/0285884 A1    Oct. 8, 2015

(51) Int. Cl.
*A61B 5/00* (2006.01)
*A61B 5/055* (2006.01)
(Continued)

(52) U.S. Cl.
CPC .......... *A61B 5/0073* (2013.01); *A61B 5/0044* (2013.01); *A61B 5/055* (2013.01); *G01R 33/4835* (2013.01); *A61B 5/0037* (2013.01); *A61B 5/7292* (2013.01); *A61B 2576/023* (2013.01); *G01R 33/4818* (2013.01); *G01R 33/4838* (2013.01); *G01R 33/5635* (2013.01)

(58) Field of Classification Search
CPC ..... A61B 5/0073; A61B 5/0044; A61B 5/055; A61B 5/0037; A61B 5/7292; A61B 2576/023; G01R 33/4835; G01R 33/4818; G01R 33/4838; G01R 33/5635
See application file for complete search history.

(56) References Cited

U.S. PATENT DOCUMENTS

2007/0205769 A1* 9/2007 Yui .................... G01R 33/5614
                                                          324/318

OTHER PUBLICATIONS

Cerqueira, Manuel D. et al; "Standardized Myocardial Segmentation and Nomenclature for Tomographic Imaging of the Heart"; Circulation 2002; 105;539-542.
(Continued)

*Primary Examiner* — Gregory H Curran

(57) ABSTRACT

A method for operating a Magnetic Resonance (MR) imaging system including generating radio frequency (RF) excitation pulses in a volume of patient anatomy that includes a patient's heart to provide subsequent acquisition of associated RF echo data and generating slice select magnetic field gradients for phase encoding and readout RF data acquisition in the volume of patient anatomy. The method also includes acquiring a plurality of slices of an image of the volume of patient anatomy within a plurality of cycles representing time period between successive beats of the patient's heart. The method also includes causing, by a control processor, accelerated acquisition of two or more slices of the plurality of slices within a quiescent phase of each of the plurality of cycles. The method further includes applying, by the control processor, one or more saturation areas proximate to a target volume of the patient anatomy.

17 Claims, 12 Drawing Sheets

(51) Int. Cl.
*G01R 33/483* (2006.01)
*G01R 33/48* (2006.01)
*G01R 33/563* (2006.01)

(56) References Cited

OTHER PUBLICATIONS

Lu, Xiaoguang, et al. "Automatic view planning for cardiac MRI acquisition." Medical Image Computing and Computer-Assisted Intervention—MICCAI 2011. Springer Berlin Heidelberg, 2011. 479-486.
Kellman et al, "Automatic LV localization and view planning for cardiac MRI acquistion", Journal of Cardiovascular Magnetic Resonance 2011, 13(Suppl 1): p. 39.
Hayes et al, "Fully automatic planning of the long-axis views of the heart", Journal of Cardiovascular Magnetic Resonance 2013, 15(Suppl 1):054.

* cited by examiner

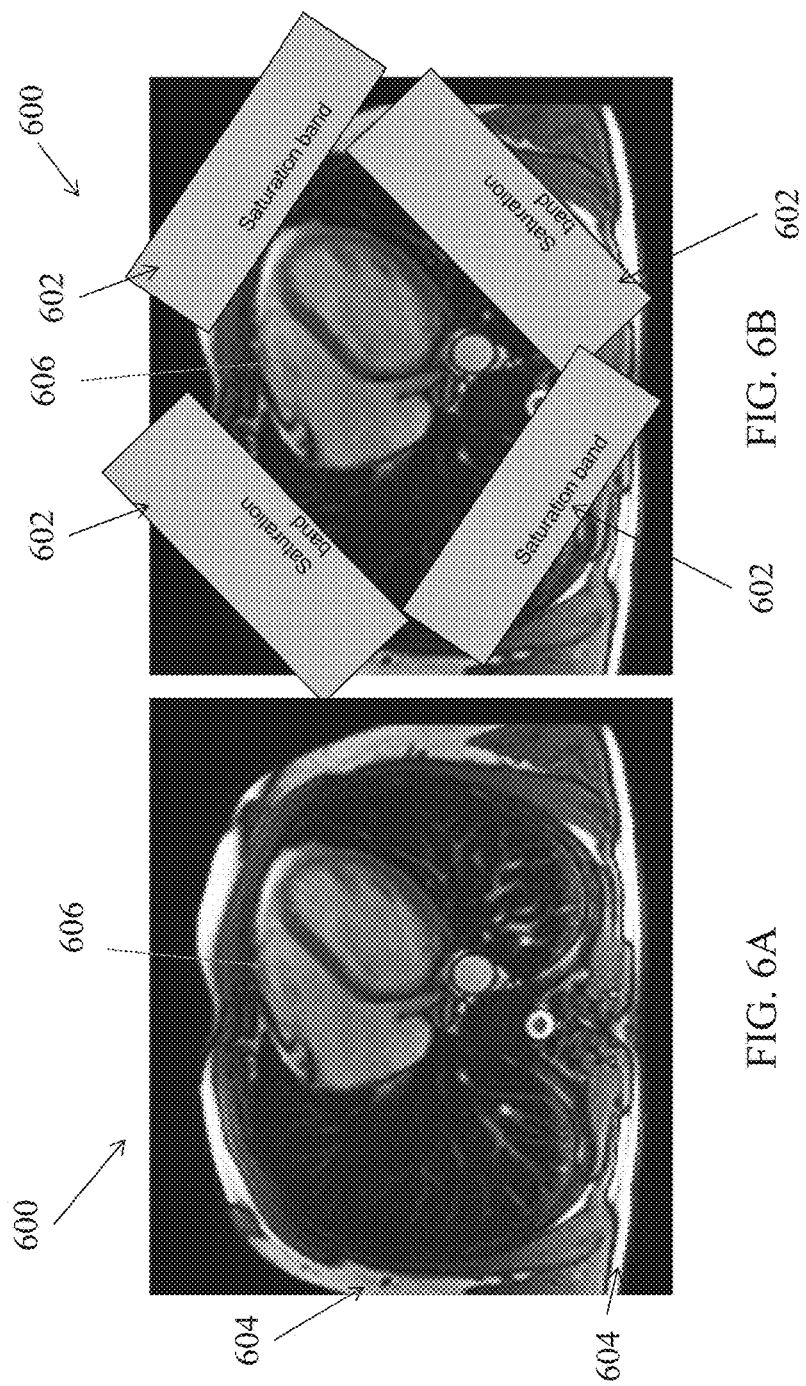

METHODS AND SYSTEMS FOR ACQUIRING MULTIPLE INTERLEAVED SLICES IN MAGNETIC RESONANCE IMAGING

TECHNOLOGY FIELD

The present application relates generally to methods, systems, and apparatuses for cardiac imaging using a Magnetic Resonance (MR) imaging system, and in particular, to methods, systems, and apparatuses for producing cardiac images using interleaved accelerated radial imaging, saturation bands and prior approximate localization of a heart.

BACKGROUND

Magnetic resonance (MR) imaging is a medical imaging technique that uses an applied magnetic field and radio frequency (RF) pulses to make images (e.g., via slices) of organs and structures inside the body. During MR imaging, the magnetic field causes magnetic field vectors of protons (typically in hydrogen atoms) to align with the magnetic field. The RF pulses cause the magnetic field vectors of the protons to be displaced (e.g., rotate) relative to the magnetic field and re-align with the magnetic field. An MRI scanner picks up signals from the protons in the body that result from magnetization field vectors re-aligning with the magnetic field. The signals may then be converted into images based on the location and strength of the incoming signals.

Cardiac Magnetic Resonance (CMR) imaging is widely used in the evaluation of many cardiac conditions. Current routine practice entails acquisition of tomographic images in planes, such as short and long axis views defined by the American Heart Association (AHA). Accordingly, an initial step in a patient examination using CMR includes identification of these tomographic planes. Typically, this process takes several manual steps by the operator, however, which is inefficient and increases operator workflow.

SUMMARY

Embodiments provide a method for operating a Magnetic Resonance (MR) imaging system that includes generating radio frequency (RF) excitation pulses in a volume of patient anatomy that includes a patient's heart to provide subsequent acquisition of associated RF echo data and generating slice select magnetic field gradients for phase encoding and readout RF data acquisition in the volume of patient anatomy. The method also includes acquiring a plurality of slices of an image of the volume of patient anatomy within a plurality of cycles. Each of the plurality of cycles represents a time period between successive beats of the patient's heart. The method also includes causing, by a control processor, accelerated acquisition of two or more slices of the plurality of slices within a quiescent phase of each of the plurality of cycles. The method further includes applying, by the control processor, one or more saturation areas proximate to a target volume of the patient anatomy.

According to one embodiment, the target volume of the patient anatomy is the patient's heart.

According to one embodiment, causing accelerated acquisition of the two or more slices within the quiescent phase of each of the plurality of cycles further includes undersampling the two or more acquired slices.

In one embodiment, the method further includes performing a pre-scan of the volume of patient anatomy prior to acquiring the plurality of slices of an image, using data from the pre-scan to determine positions of the one or more saturation areas proximate to target volume of the patient anatomy and acquiring the two or more slices of the image having the one or more saturation areas at the determined positions.

In one aspect of an embodiment, the method further includes determining the positions of the one or more saturation areas by detecting a boundary of the target volume of the patient anatomy in the pre-scan and positioning the one or more saturation areas at the edge of the detected boundary of the target volume of the patient anatomy.

In another aspect of an embodiment, the detecting the boundary of the target volume of the patient anatomy further includes analyzing pixel intensity distribution across the image of the pre-scan and determining whether the pixel intensity of the target volume of the patient anatomy and the pixel intensity of the volume of patient anatomy proximate to the target volume of the patient anatomy is equal to or within a predetermined pixel intensity threshold.

According to one embodiment, the method further includes interleaving the plurality of slices of the image acquired within the quiescent phase of each of the plurality of cycles.

According to one embodiment, interleaving the plurality of slices includes acquiring the slices with similar intensity levels consecutively within the quiescent phase of each of the plurality of cycles. In an aspect of an embodiment, N number of slices are acquired within the plurality of cycles, n number of slices are acquired within the quiescent phase of each of the plurality of cycles and the plurality of slices are acquired within the quiescent phase of each kth cycle in the order of k, (k+N/n), (k+2*N/n).

Embodiments provide a multi-slice, magnetic resonance (MR) imaging system, that includes a radio frequency (RF) signal generator configured to generate RF excitation pulses in a volume of patient anatomy including a patient's heart and enabling subsequent acquisition of associated RF echo data. The system also includes a magnetic field gradient generator configured to generate slice select magnetic field gradients for phase encoding and readout RF data acquisition in the volume of patient anatomy and a plurality of RF coils configured to acquire a plurality of slices of an image of the volume of patient anatomy within a plurality of cycles, each of the plurality of cycles representing time period between successive beats of the patient's heart. The method further includes a controller configured to cause: (i) the plurality of RF coils to acquire two or more of the plurality of slices within a quiescent phase of each of the plurality of cycles; and (ii) one or more saturation areas to be applied proximate to a target volume of the patient anatomy.

According to one embodiment, the target volume of the patient anatomy is the patient's heart.

According to another embodiment, causing the acquisition of the two or more slices within the quiescent phase of each of the plurality of cycles further includes causing accelerated acquisition of the two or more slices by undersampling the two or more slices.

In yet another embodiment, the controller is further configured to use data from a pre-scan of the volume of patient anatomy to determine positions of the one or more saturation areas proximate to the target volume of the patient anatomy and acquire the two or more imaging slices of the image having the one or more saturation areas at the determined positions.

In one aspect of an embodiment, the controller is further configured to determine the positions of the one or more saturation areas by detecting a boundary of the target volume of the patient anatomy in the pre-scan and position the one or more saturation areas at the edge of the detected boundary of the target volume of the patient anatomy.

In another aspect of an embodiment, the controller is further configured to detect the boundary of the patient's heart by analyzing pixel intensity distribution across the image of the pre-scan and determine whether the pixel intensity of the target volume of the patient anatomy and the pixel intensity of the volume of anatomy proximate to the target volume of the patient anatomy is equal to or within a predetermined pixel intensity threshold.

According to another embodiment, the controller is further configured to cause the plurality of RF coils to acquire the plurality of slices of the image by interleaving the plurality of slices of the image and acquire consecutive slices with similar intensity levels consecutively within the quiescent phase of each of the plurality of cycles.

Embodiments provide an article of manufacture for operating a multi-slice, multi-segment magnetic resonance (MR) imaging system, the article of manufacture including a non-transitory, tangible computer-readable medium holding computer-executable instructions for performing a method that includes generating radio frequency (RF) excitation pulses in a volume of patient anatomy comprising a heart to provide subsequent acquisition of associated RF echo data and generating slice select magnetic field gradients for phase encoding and readout RF data acquisition in the volume of patient anatomy.

According to one embodiment, the medium holds computer-executable instructions for performing a method that further includes acquiring a plurality of slices of an image of the volume of patient anatomy within a plurality of cycles. Each of the plurality of cycles represent a time period between successive beats of the patient's heart. The medium holds computer-executable instructions for performing a method that further includes causing, by a control processor, accelerated acquisition of two or more slices of the plurality of slices within a quiescent phase of each of the plurality of cycles and applying, by the control processor, one or more saturation areas proximate to a target volume of the patient anatomy.

According to one embodiment, causing the acquisition of the two or more slices within the quiescent phase of each of the plurality of cycles further includes causing accelerated acquisition of the two or more slices by under sampling the two or more slices.

According to another embodiment, the medium holds computer-executable instructions for performing a method that further includes using data from a pre-scan of the volume of patient anatomy to determine positions of the one or more saturation areas proximate to the target volume of the patient anatomy and acquiring the two or more slices of the image having the one or more saturation areas at the determined positions.

In yet another embodiment, the medium holds computer-executable instructions for performing a method that further includes determining the positions of the one or more saturation areas by detecting a boundary of the target volume of the patient anatomy in the pre-scan and positioning the one or more saturation areas at the edge of the detected boundary of the target volume of the patient anatomy.

BRIEF DESCRIPTION OF THE DRAWINGS

The foregoing and other aspects of the present invention are best understood from the following detailed description when read in connection with the accompanying drawings.

For the purpose of illustrating the invention, there is shown in the drawings embodiments that are presently preferred, it being understood, however, that the invention is not limited to the specific instrumentalities disclosed. Included in the drawings are the following Figures:

FIG. 6A is an image of a volume of patient anatomy illustrating a patient's heart and bright background tissue areas proximate to the patient's heart, for use with embodiments disclosed herein;

FIG. 6B illustrates saturation areas over the bright background tissue areas of the image shown in FIG. 6A according to embodiments of the present invention;

DETAILED DESCRIPTION OF EXEMPLARY EMBODIMENTS

Conventional automated two-dimensional imaging methods of obtaining and displaying the cardiac planes from a set of MR images covering the entire heart may not acquire certain data in a single measurement step for various reasons. For example, because MR imaging is sensitive to cardiac and breathing motions, the data is typically acquired only during a quiescent phase (e.g., 250 milliseconds during diastole) of each cardiac cycle when the heart is relatively motionless. To acquire high resolution (spatial) images covering the entire heart, patients may need to hold their breath for many cycles (e.g., 50 heartbeats) to minimize respiratory motion artifacts. Sufficiently high quality and spatial resolution (e.g., voxel sizes of 3 mm or finer sizes) of the images are also typically used to provide precise and accurate automatic segmentation/detection. Further, the entire heart is typically covered by the images to identify all the standard planes.

Some conventional CMR imaging methods use accelerated three-dimensional imaging. While theses conventional accelerated three-dimensional imaging methods may reduce acquisition time, these three-dimensional imaging methods techniques are very sensitive to motion such as respiratory drift.

Embodiments of the present invention efficiently reconstruct MR images with full anatomical coverage of the heart by acquiring multiple two-dimensional interleaved slices during the quiescent mid-diastolic cardiac phase. Subsequently reconstructed and reformatted 3D images of the heart provide an initial morphologic assessment or generate standard cardiac views either manually or by the use of automatic segmentation and detection algorithms.

Embodiments of the present invention include systems and methods of cardiac imaging that acquire a high resolution snapshot of the entire heart in a single-step, thereby reducing the overall scan time per patient, and streamlining the clinical workflow. Embodiments of the present invention provide images of quality sufficient to permit automatic detection of anatomical landmarks and calculation of standard cardiac planes. According to one embodiment, images are acquired using a target in-plane spatial resolution of 1 mm and a target through-plane resolution of 2-3 mm for visualization of standard heart planes.

Embodiments of the present invention streamline the workflow of cardiac MR imaging by rapidly acquiring the data to identify and display cardiac planes. Embodiments of the present invention may provide a quick assessment of cardiac morphology prior to a more detailed image acquisition. Embodiments of the present invention may be used to acquire images of any volume of patient anatomy including a patient's heart. Embodiments of the present invention may be used in rapid and high resolution mapping of pulmonary veins for electrophysiology applications.

Figure 1:
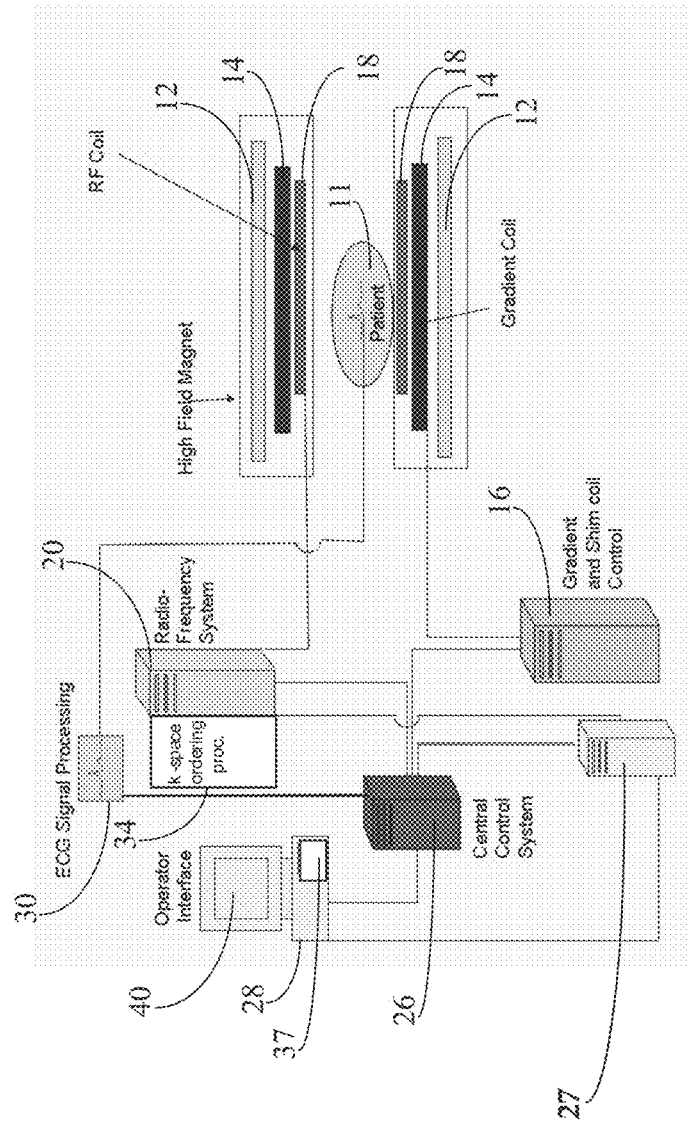
FIG. 1 is a system block diagram illustrating a system for acquiring multiple interleaved slices in MR imaging, for use with embodiments disclosed herein.

FIG. 1 is a system block diagram illustrating a system 10 for acquiring multiple interleaved slices in MR imaging, for use with embodiments disclosed herein. As shown at FIG. 1, system 10 includes a magnet 12 configured to create a static magnetic field in the body of patient 11 to be imaged and positioned on a table. System 10 also includes a plurality of coils 14 that include gradient coils and shimming coils configured to produce position dependent magnetic field gradients superimposed on the static magnetic field. The gradient coils are configured to generate linear slice select magnetic field gradients on a static magnetic field. The coils 14, in response to gradient signals supplied thereto by a gradient and shimming and pulse sequence control module 16, produce position dependent and shimmed magnetic field gradients in three orthogonal directions and generate magnetic field pulse sequences. The shimming coils are configured to generate non-linear magnetic field gradients on the static magnetic field to modify the homogeneity of the static magnetic field. That is, the shimmed gradients compensate for non-homogeneity and variability in an MR imaging device magnetic field resulting from patient anatomical variation and other sources. The magnetic field gradients include a slice-selection gradient magnetic field, a phase encoding gradient magnetic field and a readout gradient magnetic field that are applied to patient 11.

Further, radio frequency (RF) module 20 provides RF pulse signals to RF coils 18, which in response produce magnetic field pulses which rotate the spins of the protons in the imaged body 11 by ninety degrees or by one hundred and eighty degrees for so-called "spin echo" imaging, or by angles less than or equal to 90 degrees for so-called "gradient echo" imaging. Pulse sequence control module 16, in conjunction with RF module 20 as directed by central control unit 26, control slice-selection, phase encoding, readout gradient magnetic fields, radio frequency transmission, and magnetic resonance signal detection to acquire magnetic resonance signals representing planar slices of patient 11.

In response to applied RF pulse signals, the RF coils 18 receive MR signals. For example, RF coils 18 may receive signals from the excited protons within the body as they return to an equilibrium position established by the static and gradient magnetic fields. The MR signals are detected and processed by a detector within RF module 20 and k-space component processor unit 34 to provide image representative data to an image data processor in central control unit 26. In some embodiments, the image data processor (e.g., image data processor 27) may be external to the central control unit 26. Electrocardiogram (ECG) synchronization signal generator 30 provides ECG signals used for pulse sequence and imaging synchronization. A two or three dimensional k-space storage array of individual data elements in unit 34 stores corresponding individual frequency components that includes a MR dataset.

A RF signal generator comprising module 20 and RF coils 18 generates RF excitation pulses in anatomy of patient 11 and enables subsequent acquisition of associated RF echo data. A magnetic field gradient generator (comprising magnetic coils 12 and 14) generates a magnetic field for use in acquiring multiple individual frequency components and generates magnetic field gradients for anatomical slice selection, phase encoding and readout RF data acquisition in a three dimensional (3D) anatomical volume. The RF signal generator units 18 and 20 and the magnetic field gradient generator units 12 and 14 provide a rotating frame preparation pulse sequence comprising at least one of: (a) a T1 spin lattice relaxation in a rotating frame (T1ρ) preparation pulse sequence of adiabatic pulses comprising modulated RF pulses and modulated magnetic field gradients for slice selection; and (b) a T2 spin-spin relaxation in a rotating frame (T2ρ) preparation pulse sequence of adiabatic pulses comprising modulated RF pulses and modulated magnetic field gradients for slice selection.

Central control unit 26 uses information stored in an internal database to process the detected MR signals in a coordinated manner to generate high quality images of a selected slice (or slices) of the body and adjusts other parameters of system 10. The stored information comprises predetermined pulse sequence and magnetic field gradient and strength data, as well as data indicating timing, orientation and spatial volume of gradient magnetic fields to be applied in imaging. Generated images are presented on display 40. Computer 28 includes a graphical user interface (GUI) enabling user interaction with central controller 26 and enables user modification of magnetic resonance imaging signals in substantially real time. Display processor 37 processes the magnetic resonance signals to provide image representative data for display on display 40, for example.

Figure 2:
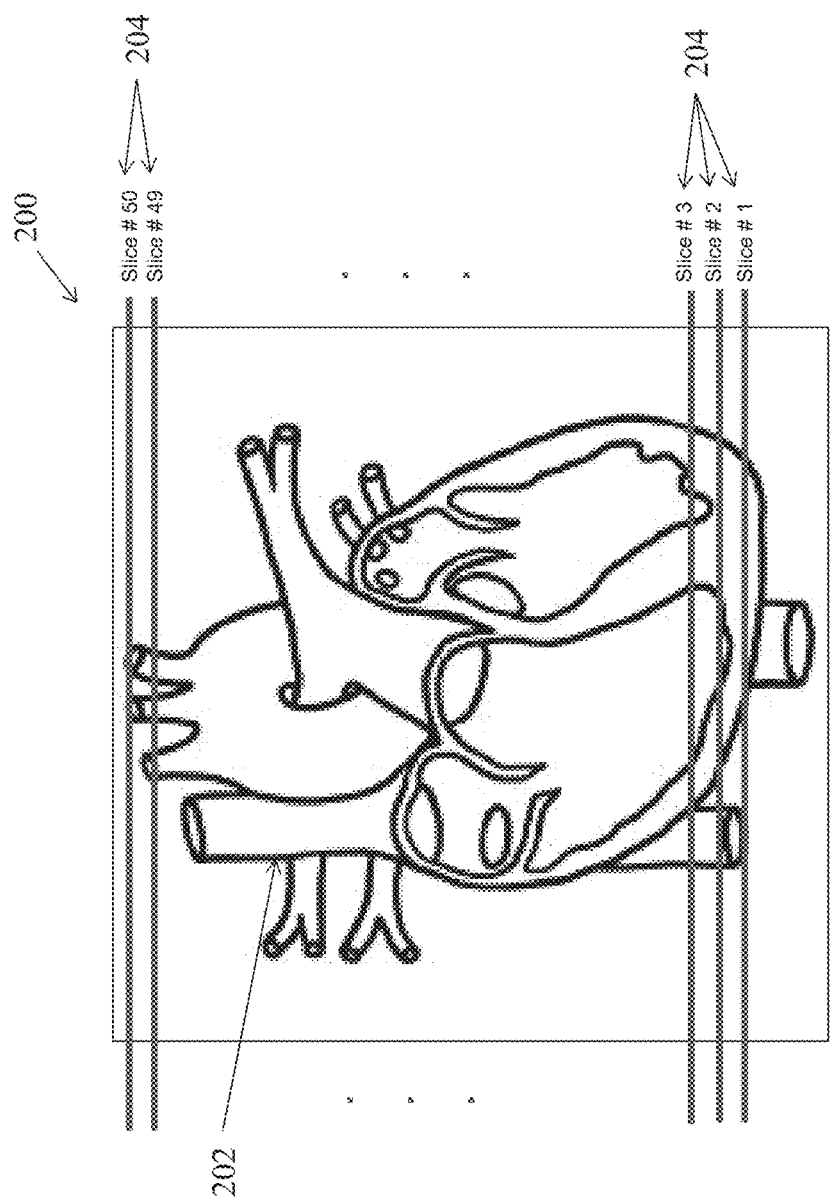
FIG. 2 is an illustration of a heart showing MR image data acquired in slices according to embodiments of the invention.

FIG. 2 is an illustration 200 of a heart 202 showing MR image data acquired in slices 204 according to embodiments of the invention. MR image data acquisition of a three-dimensional object (e.g., a heart) is accomplished slice-by-slice, starting from either the top or bottom end of the heart. As shown in FIG. 2, the image of heart 202 is acquired in slices, starting with slice #1 and ending with slice #50.

Figure 3A:
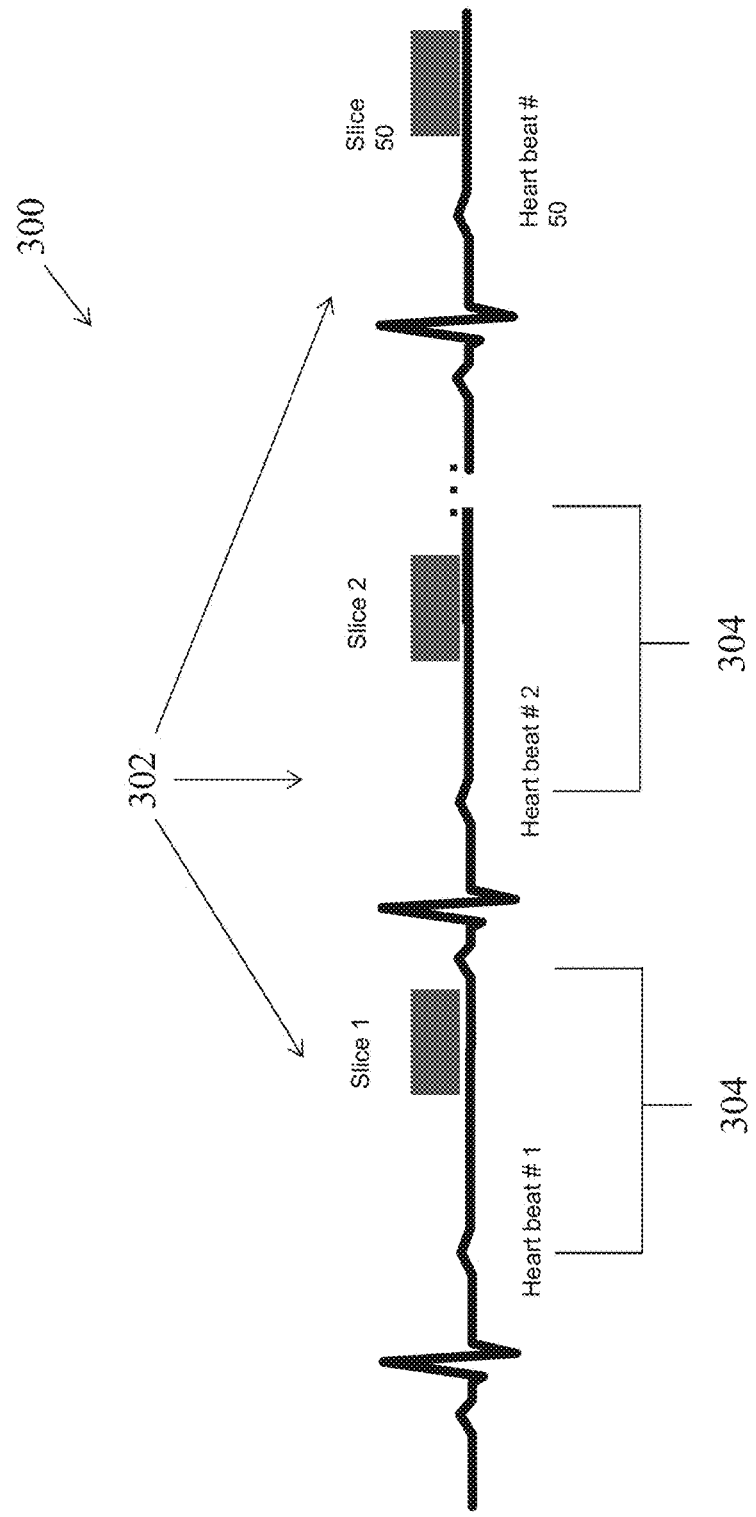
FIG. 3A is an illustration showing a single slice of an image acquired during each of a plurality of cycles.

FIG. 3A is an illustration 300 showing acquisition of a single slice of an image during each of cycles 302. Because the sensitivity of MR images to motion, data acquisition is generally restricted to quiescent phase (e.g., mid-diastolic) of a cardiac cycle when the heart is relatively motionless. Therefore, conventional CMR imaging methods acquire a single slice of data during the quiescent phase of each heart-beat. As shown in FIG. 3A, slice 1 is acquired during a quiescent phase 304 of a first cycle (heartbeat #1) of cycles 302, slice 2 is acquired during quiescent phase 304 of a second cycle (heartbeat #2) of cycles 302, and subsequent slices are acquired during respective quiescent phases of subsequent cycles 302 until the last slice 50 is acquired during quiescent phase 304 of the 50$^{th}$ cycle (heartbeat #50) of cycles 302.

The number of slices and cycles shown in FIG. 3A is merely exemplary and is based on the image acquisition for an average adult heart. Typically, to cover an average adult heart, with each slice being 2-3 mm thick, a data acquisition period of approximately 50 heartbeats is used. Other data acquisition periods may, however, be used. During the period of approximately 50 heartbeats, patients hold their breath to avoid image degradation due to breathing motion, which is often difficult and outside the scope of most patients.

Figure 3B:
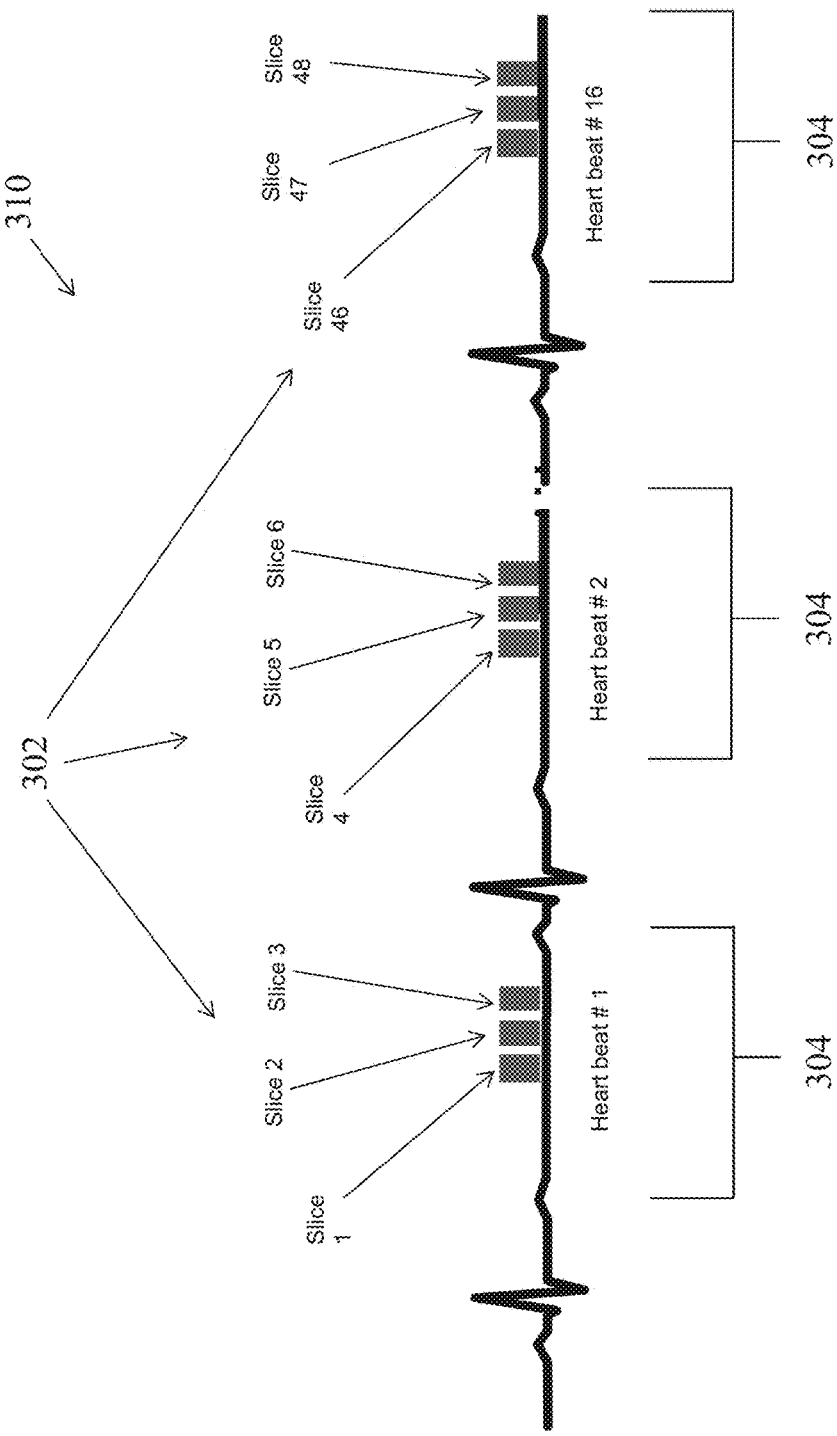
FIG. 3B is an illustration showing multiple slices of an image acquired during each of the plurality of cycles shown in FIG. 3A according to embodiments of the present invention.

FIG. 3B is an illustration 310 showing acquisition of multiple slices (slices 1-6 and 46-48) of an image of a patient's heart during each of cycles 302 according to embodiments of the present invention. As shown in FIG. 3B, two-dimensional interleaved slices 1-3 may be acquired during a quiescent phase 304 of a first cycle (heartbeat #1) of cycles 302, two-dimensional interleaved slices 4-6 may be acquired during a quiescent phase 304 of a second cycle (heartbeat #2) of cycles 302, and subsequent slices are acquired during respective quiescent phases of subsequent cycles 302 until two-dimensional interleaved slices 46-48 may be acquired during a quiescent phase 304 of a sixteenth cycle (heartbeat #16) of cycles 302. The acquisition time per cycle shown in FIG. 3A remains the same as the acquisition time per cycle shown in FIG. 3B.

As described above, acquiring data (slices) outside of the quiescent diastolic phases 304 of each cycle 302 may be problematic because of the sensitivity of MR images to motion. Because the data acquisition of multiple slices may potentially extend beyond quiescent diastolic phases 304, embodiments of the invention use accelerated imaging to acquire multiple slices within each quiescent diastolic phases 304. For example, as shown in FIG. 3B, slice 1, slice 2 and slice 3 are acquired within heart beat #1. Slice 4, slice 5 and slice 6 are acquired in heart beat #2. The sequence continues until slice 46, slice 47 and slice 48 are acquired within heart beat #16. In some aspects, the accelerated imaging may include under-sampled radial imaging to permit high spatial resolution without significant increase in scan time. Aspects may, however, include other types of accelerated imaging.

The accelerated acquisition reduces the total acquisition time for the image of heart 200. Accordingly, the acquisition of multiple slices (e.g., any plurality of slices including each slice) may be accomplished in less time (e.g., 48 slices of an image in 16 cycles as shown in FIG. 3B) than when a single slice is acquired per heart-beat (e.g., 50 slices in 50 cycles as shown in FIG. 3A).

Figure 4:
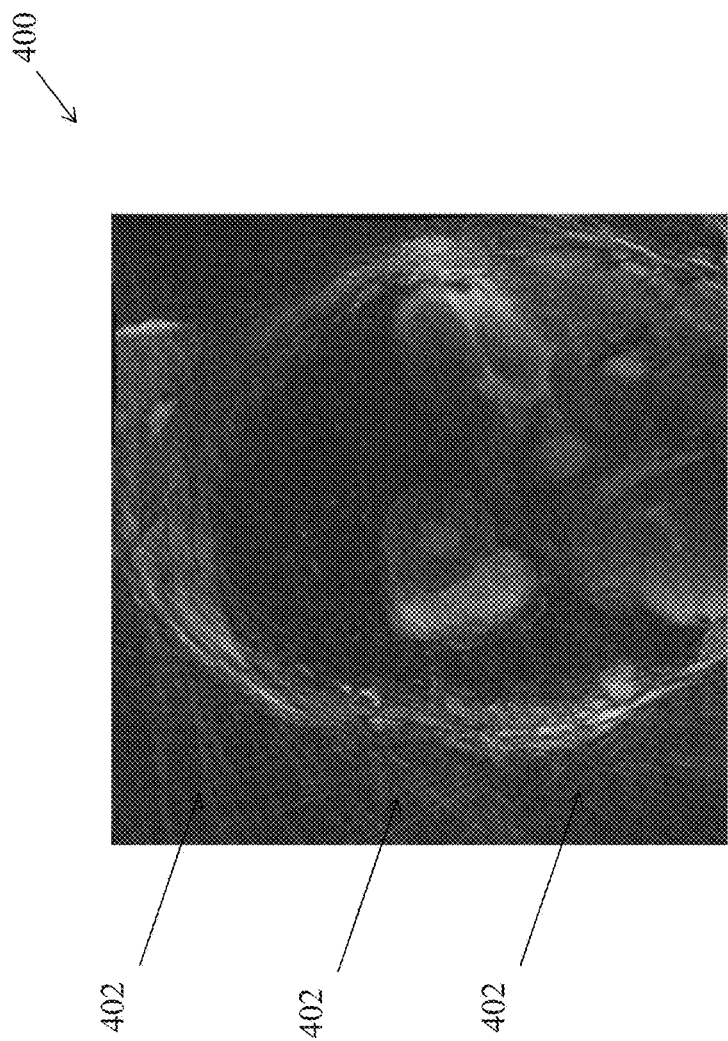
FIG. 4 shows an image of patient anatomy having streaking artifacts that may degrade image quality.

Accelerated acquisition using radial imaging may, however, degrade image quality. For example, image quality may be degraded by streaking artifacts. FIG. 4 shows an image 400 of streaking artifacts 402 that arise due to high under-sampling of data acquisition. As shown in FIG. 4, background regions that should be black, are instead, represented by streaking artifacts 402.

Figure 5B:
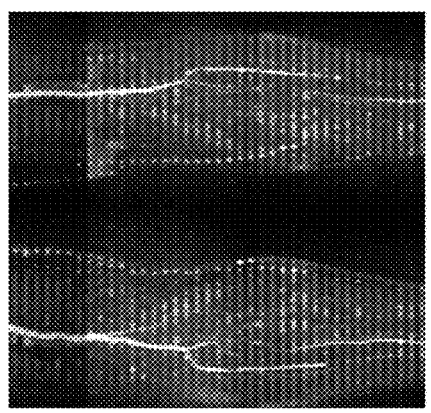
FIGS. 5A and 5B are multi-planar reconstruction images generated from a stack of sequentially acquired slices of patient anatomy illustrating venetian-blind artifacts.
Figure 5A:

Image quality may also be degraded by a "venetian-blind artifact." When multiple adjacent slices are acquired in rapid succession, the slice that is acquired later has a lower signal due to saturation effects from the previous slice. Accordingly, when such slices are stacked together, the resulting stack may produce a "venetian-blind artifact", as shown in the image 500 at FIG. 5A and image 510 at FIG. 5B. To prevent the venetian blind artifact, embodiments of the invention may use an interleaved slice acquisition order, whereby slices that are spatially separated are acquired within the same heartbeat. Interleaving the acquisition of slices may improve the recovery from saturation of adjacent slices, which are acquired in the next heartbeat, providing high resolution and high signal to noise ratio (SNR) images. When these multiple slices are stacked together and reformatted, the resulting 3D stack accurately depicts cardiac anatomy. In some embodiments, the resulting images may be input to automatic algorithms that detect standard cardiac planes.

FIG. 6A shows an image 600 of a volume of an anatomy that includes a patient's heart 606 and bright background tissue areas 604 proximate to the patient's heart 606. FIG. 6B show saturation areas 602 (e.g., saturation bands) over the bright background tissue areas 604 of the image 600 shown in FIG. 6A. Embodiments of the invention mitigate streaking by saturating the bright background tissue areas 604, thereby suppressing the signal from the bright background tissue areas 604. For example, the saturation areas 602 shown in FIG. 6B suppress background signal from the bright background tissue areas 604 which would otherwise cause streaking into the target volume of patient anatomy, such as the patient's heart 606 shown in FIG. 6B.

In one aspect, the volume of patient anatomy within the available field of view may be pre-scanned and the saturation areas 602 may be positioned either manually or automatically on the resultant images. Such pre-scans or adjustment scans are typically performed for the patient at the beginning of an imaging session prior to the acquisition of images of the patient's target volume of anatomy (e.g., heart). The adjustment scan may be a low spatial resolution 2D or 3D acquisition used for initial calibration of magnetic field shimming and frequency adjustments, and typically covers a larger volume of the patient's anatomy than the target volume of anatomy (e.g., heart 606 shown in FIG. 6B) of the patient.

Figure 7:
FIG. 7 illustrates an improvement in image quality over the image shown in FIG. 4 by the use of the saturation bands according to embodiments of the present invention.

In another aspect, body boundary detection may be used to determine the positions of the saturation bands proximate to the target volume of patient anatomy, such as the positions of the saturation bands proximate to the heart, as shown in FIG. 6B. The determination of the saturation band positions may include detecting a boundary of the target volume of anatomy in the adjustment scan and positioning the saturation bands at the edge of the detected boundary of the target volume of anatomy. The detection of the boundary of the target volume of anatomy may include analyzing pixel intensity distribution across the pre-scan images and determining whether the pixel intensity of the target volume of anatomy (e.g., heart) and the pixel intensity of the volume of anatomy proximate to the target volume of anatomy (e.g., background) is equal to or within a predetermined pixel intensity threshold. The pixel intensities may include intensities of two-dimensional pixels or three-dimensional voxels. Connected component analysis may then be applied to determine the largest background block. For example, the border of the thorax may be determined accordingly. FIG. 7 is the image 400 of the patient's heart shown in FIG. 4 illustrating an improvement in image quality by the use of the saturation bands 602 shown in FIG. 6.

Although the target area in the embodiment shown in FIG. 6B is a patient's heart, embodiments may include target areas of any portion of patient anatomy and may include one or more saturation areas applied proximate to any volume of the patient anatomy.

Figure 8:
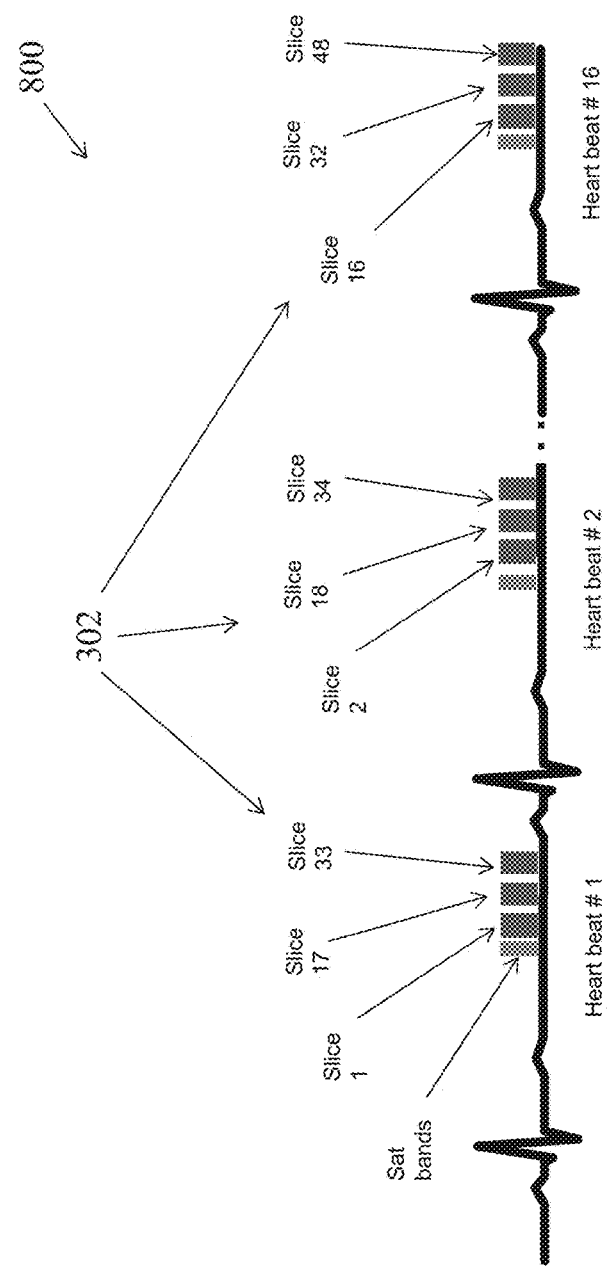
FIG. 8 is an illustration showing an exemplary method of interleaving slices of an image according to embodiments of the present invention.
Figure 9B:
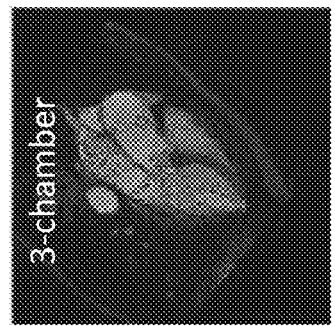
FIGS. 9A through 9D are images of four standard cardiac views reformatted automatically from data acquired using the embodiments described herein.
Figure 9D:
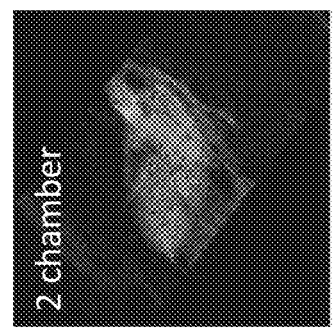
Figure 9A:
Figure 9C:
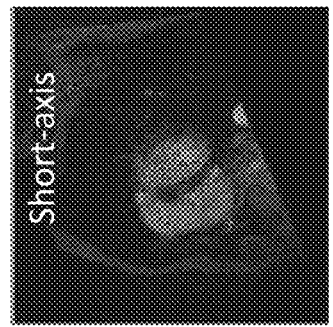

FIG. 8 is an illustration 800 showing an exemplary method of interleaving slices of an image. According to the exemplary interleaving method shown in FIG. 8, N slices are acquired for the plurality of cycles 302 and n slices are acquired for each cycle (heartbeat) 302. Accordingly, slices are acquired for N/n cycles. For each kth cycle, the slices to be acquired in the order of: k, (k+N/n), (k+2*N/n). In the exemplary interleaving method shown in FIG. 8, N=48 total slices, n=3 slices acquired for each cycle (e.g., heartbeat) and N/n=16 cycles. Therefore, slices 1, 17 and 33 are acquired during the first heartbeat. Slices 2, 18 and 34 are acquired during the second heartbeat and the sequence continues until each of the plurality of slices N are acquired for each of the plurality of cycles N/n. That is, in the embodiment shown in FIG. 8, the sequence continues until slice 16, slice 32 and slice 48 are acquired during the sixteenth heartbeat.

The method of interleaving shown in FIG. 8 is merely exemplary. Embodiments may include other interleaving methods. For example, interleaving methods may include regular sequential acquisition and random acquisition. Sequential acquisition and random acquisition may still result in consecutive acquisition of the slices, however, and the localized venetian blind artifact may still occur and the resulting images may not be of high quality. The interleaving method shown in FIG. 8 acquires the slices such that slices with similar intensity levels are physically next to each other. That is, interleaving of the slices includes consecutively acquiring slices having similar intensity levels within the quiescent phase of each of the plurality of cycles, thereby providing higher quality images.

FIGS. 9A to 9D are images of four standard cardiac planes reformatted automatically from data acquired using the embodiments described herein. Efficient, high quality images may also be used to automate prescription of other standard cardiac views to substitute the lengthy planning process in current clinical practice.

Figure 10:
FIG. 10 is an image of a patient's heart illustrating a pathological cyst determined using the embodiments described herein.

FIG. 10 is an image 1000 of a patient's heart illustrating a pathological cyst. The precise location of the pathologies, such as cyst 1002 shown in FIG. 10 and morphological assessment of the cardiac anatomy may be determined using the embodiments described herein that produce efficient high quality images.

Figure 11:
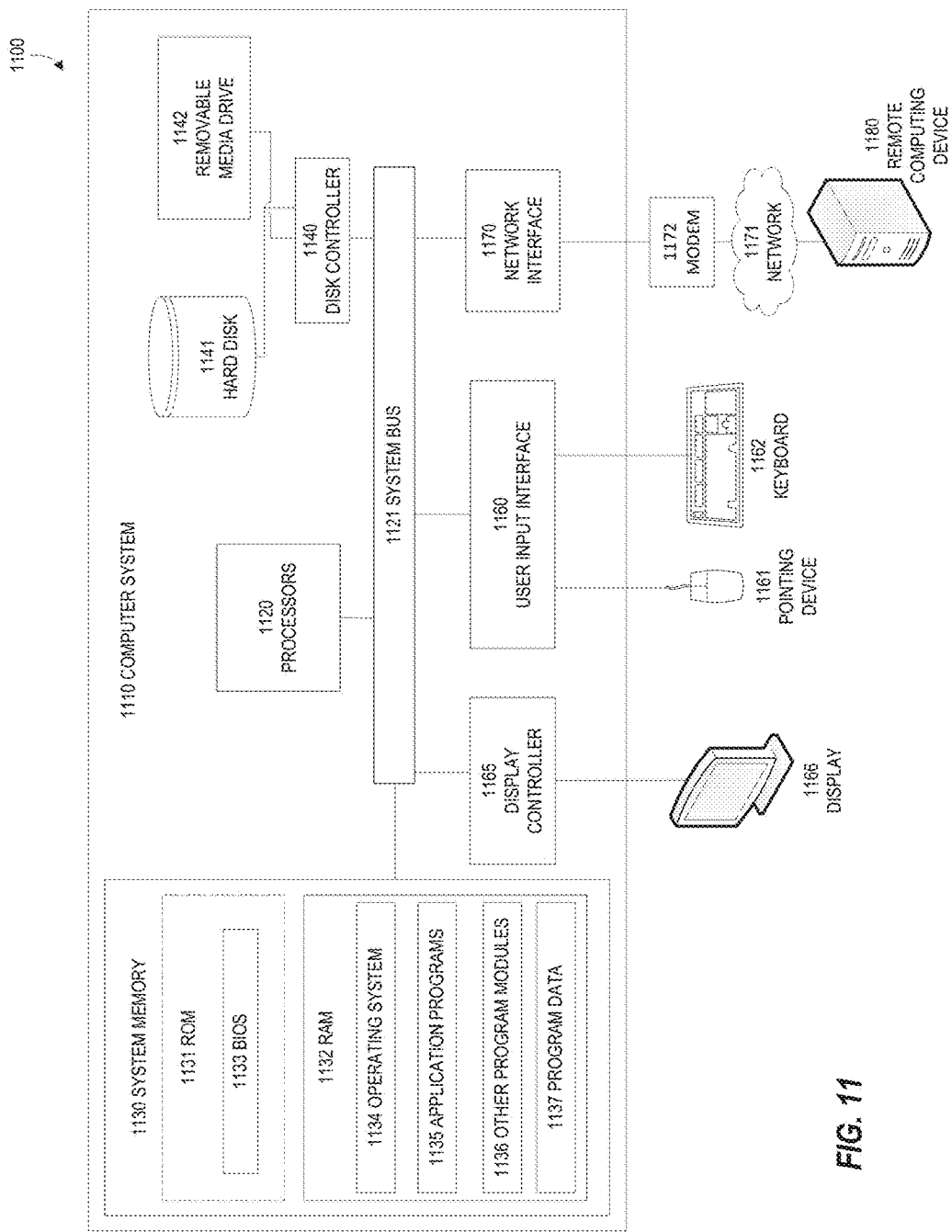
FIG. 11 illustrates an example of a computing environment within which embodiments of the invention may be implemented.

FIG. 11 illustrates an example of a computing environment 1100 within which embodiments of the invention may be implemented. Computing environment 1100 may include computer system 1110, which is one example of a computing system upon which embodiments of the invention may be implemented. As shown in FIG. 11, the computer system 1110 may include a communication mechanism such as a bus 1121 or other communication mechanism for communicating information within the computer system 1110. The system 1110 further includes one or more processors 1120 coupled with the bus 1121 for processing the information. The processors 1120 may include one or more CPUs, GPUs, or any other processor known in the art.

The computer system 1110 also includes a system memory 1130 coupled to the bus 1121 for storing information and instructions to be executed by processors 1120. The system memory 1130 may include computer readable storage media in the form of volatile and/or nonvolatile memory, such as read only memory (ROM) 1131 and/or random access memory (RAM) 1132. The system memory RAM 1132 may include other dynamic storage device(s) (e.g., dynamic RAM, static RAM, and synchronous DRAM). The system memory ROM 1131 may include other static storage device(s) (e.g., programmable ROM, erasable PROM, and electrically erasable PROM). In addition, the system memory 1130 may be used for storing temporary variables or other intermediate information during the execution of instructions by the processors 1120. A basic input/output system (BIOS) 1133 containing the basic routines that help to transfer information between elements within computer system 1110, such as during start-up, may be stored in ROM 1131. RAM 1132 may contain data and/or program modules that are immediately accessible to and/or presently being operated on by the processors 1120. System memory 1130 may additionally include, for example, operating system 1134, application programs 1135, other program modules 1136 and program data 1137.

The computer system 1110 also includes a disk controller 1140 coupled to the bus 1121 to control one or more storage devices for storing information and instructions, such as a magnetic hard disk 1141 and a removable media drive 1142 (e.g., floppy disk drive, compact disc drive, tape drive, and/or solid state drive). The storage devices may be added to the computer system 1110 using an appropriate device interface (e.g., a small computer system interface (SCSI), integrated device electronics (IDE), Universal Serial Bus (USB), or FireWire).

The computer system 1110 may also include a display controller 1165 coupled to the bus 1121 to control a display or monitor 1166, such as a cathode ray tube (CRT) or liquid crystal display (LCD), for displaying information to a computer user. The computer system includes an input interface 1160 and one or more input devices, such as a keyboard 1162 and a pointing device 1161, for interacting with a computer user and providing information to the processor 1120. The pointing device 1161, for example, may be a mouse, a trackball, or a pointing stick for communicating direction information and command selections to the processor 1120 and for controlling cursor movement on the display 1166. The display 1166 may provide a touch screen interface which allows input to supplement or replace the communication of direction information and command selections by the pointing device 1161.

The computer system 1110 may perform a portion or all of the processing steps of embodiments of the invention in response to the processors 1120 executing one or more sequences of one or more instructions contained in a memory, such as the system memory 1130. Such instructions may be read into the system memory 1130 from another computer readable medium, such as a hard disk 1141 or a removable media drive 1142. The hard disk 1141 may contain one or more datastores and data files used by embodiments of the present invention. Datastore contents and data files may be encrypted to improve security. The processors 1120 may also be employed in a multi-processing arrangement to execute the one or more sequences of instructions contained in system memory 1130. In alternative embodiments, hard-wired circuitry may be used in place of or in combination with software instructions. Thus, embodiments are not limited to any specific combination of hardware circuitry and software.

As stated above, the computer system 1110 may include at least one computer readable medium or memory for holding instructions programmed according to embodiments of the invention and for containing data structures, tables, records, or other data described herein. The term "computer readable medium" as used herein refers to any non-transitory, tangible medium that participates in providing instructions to the processor 1120 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1141 or removable media drive 1142. Non-limiting examples of volatile media include dynamic memory, such as system memory 1130. Non-limiting examples of transmission media include coaxial cables, copper wire, and fiber optics, including the wires that make up the bus 1121. Transmission media may also take the form of acoustic or light waves, such as those generated during radio wave and infrared data communications.

The computing environment 1100 may further include the computer system 1110 operating in a networked environment using logical connections to one or more remote computers, such as remote computer 1180. Remote computer 1180 may be a personal computer (laptop or desktop), a mobile device, a server, a router, a network PC, a peer device or other common network node, and typically includes many or all of the elements described above relative to computer 1110. When used in a networking environment, computer 1110 may include modem 1172 for establishing communications over a network 1171, such as the Internet. Modem 1172 may be connected to system bus 1121 via user network interface 1170, or via another appropriate mechanism.

Network 1171 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1110 and other computers (e.g., remote computing system 1180). The network 1171 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1171.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The GUI also includes an executable procedure or executable application. The executable procedure or executable application conditions the display processor to generate signals representing the GUI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the GUI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of the figures presented herein are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices on a network linking the units of FIG. 5. Any of the functions and steps provided in the Figures may be implemented in hardware, software or a combination of both. No claim element herein is to be construed under the provisions of 35 U.S.C. 112, sixth paragraph, unless the element is expressly recited using the phrase "means for."

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

The invention claimed is:
1. A method for operating a Magnetic Resonance (MR) imaging system, the method comprising:
    generating radio frequency (RF) excitation pulses in a volume of patient anatomy comprising a patient's heart to provide subsequent acquisition of associated RF echo data;
    generating slice select magnetic field gradients for phase encoding and readout RF data acquisition in the volume of patient anatomy;
    acquiring a plurality of slices of an image of the volume of patient anatomy within a plurality of cycles, each of the plurality of cycles representing time period between successive beats of the patient's heart;
causing, by a control processor, accelerated acquisition of two or more slices of the plurality of slices within a quiescent phase of each of the plurality of cycles;
applying, by the control processor, one or more saturation areas proximate to a target volume of the patient anatomy; and
wherein causing accelerated acquisition of the two or more slices within the quiescent phase of each of the plurality of cycles further comprises under-sampling the two or more acquired slices.

2. The method according to claim 1, wherein the target volume of the patient anatomy is the patient's heart.

3. The method according to claim 1, further comprising:
performing a pre-scan of the volume of patient anatomy prior to acquiring the plurality of slices of an image;
using data from the pre-scan to determine positions of the one or more saturation areas proximate to target volume of the patient anatomy; and
acquiring the two or more slices of the image having the one or more saturation areas at the determined positions.

4. The method according to claim 3, further comprising:
determining the positions of the one or more saturation areas by detecting a boundary of the target volume of the patient anatomy in the pre-scan; and
positioning the one or more saturation areas at the edge of the detected boundary of the target volume of the patient anatomy.

5. The method according to claim 4, wherein detecting the boundary of the target volume of the patient anatomy further comprises:
analyzing pixel intensity distribution across the image of the pre-scan; and
determining whether the pixel intensity of the target volume of the patient anatomy and the pixel intensity of the volume of patient anatomy proximate to the target volume of the patient anatomy is equal to or within a predetermined pixel intensity threshold.

6. The method according to claim 1, further comprising interleaving the plurality of slices of the image acquired within the quiescent phase of each of the plurality of cycles.

7. The method according to claim 6, wherein interleaving the plurality of slices comprises acquiring the slices with similar intensity levels consecutively within the quiescent phase of each of the plurality of cycles.

8. The method according to claim 6, wherein, N number of slices are acquired within the plurality of cycles; n number of slices are acquired within the quiescent phase of each of the plurality of cycles; and the plurality of slices are acquired within the quiescent phase of each kth cycle in the order of k, (k+N/n), (k+2*N/n).

9. A multi-slice, magnetic resonance (MR) imaging system, comprising:
radio frequency (RF) signal generator configured to generate RF excitation pulses in a volume of patient anatomy comprising a patient's heart and enabling subsequent acquisition of associated RF echo data;
a magnetic field gradient generator configured to generate slice select magnetic field gradients for phase encoding and readout RF data acquisition in the volume of patient anatomy;
a plurality of RF coils configured to acquire a plurality of slices of an image of the volume of patient anatomy within a plurality of cycles, each of the plurality of cycles representing time period between successive beats of the patient's heart;
a controller configured to cause: (i) the plurality of RF coils to acquire two or more of the plurality of slices within a quiescent phase of each of the plurality of cycles; and (ii) one or more saturation areas to be applied proximate to a target volume of the patient anatomy; and
wherein causing the acquisition of the two or more slices within the quiescent phase of each of the plurality of cycles further comprises causing accelerated acquisition of the two or more slices by under-sampling the two or more slices.

10. The system according to claim 9, wherein the target volume of the patient anatomy is the patient's heart.

11. The system according to claim 9, wherein the controller is further configured to:
use data from a pre-scan of the volume of patient anatomy to determine positions of the one or more saturation areas proximate to the target volume of the patient anatomy; and
acquire the two or more imaging slices of the image having the one or more saturation areas at the determined positions.

12. The system according to claim 11, wherein the controller is further configured to:
determine the positions of the one or more saturation areas by detecting a boundary of the target volume of the patient anatomy in the pre-scan; and
position the one or more saturation areas at the edge of the detected boundary of the target volume of the patient anatomy.

13. The system according to claim 12, wherein the controller is further configured to detect the boundary of the patient's heart by:
analyzing pixel intensity distribution across the image of the pre-scan; and
determine whether the pixel intensity of the target volume of the patient anatomy and the pixel intensity of the volume of anatomy proximate to the target volume of the patient anatomy is equal to or within a predetermined pixel intensity threshold.

14. The system according to claim 8, wherein the controller is further configured to cause the plurality of RF coils to acquire the plurality of slices of the image by interleaving the plurality of slices of the image and acquire consecutive slices with similar intensity levels consecutively within the quiescent phase of each of the plurality of cycles.

15. An article of manufacture for operating a multi-slice, multi-segment magnetic resonance (MR) imaging system, the article of manufacture comprising a non-transitory, tangible computer-readable medium holding computer-executable instructions for performing a method comprising:
generating radio frequency (RF) excitation pulses in a volume of patient anatomy comprising a heart to provide subsequent acquisition of associated RF echo data;
generating slice select magnetic field gradients for phase encoding and readout RF data acquisition in the volume of patient anatomy;
acquiring a plurality of slices of an image of the volume of patient anatomy within a plurality of cycles, each of the plurality of cycles representing time period between successive beats of the patient's heart;
causing, by a control processor, accelerated acquisition of two or more slices of the plurality of slices within a quiescent phase of each of the plurality of cycles;

applying, by the control processor, one or more saturation areas proximate to a target volume of the patient anatomy; and wherein the method further comprises causing the acquisition of the two or more slices within the quiescent phase of each of the plurality of cycles further comprises causing accelerated acquisition of the two or more slices by under sampling the two or more slices.

16. The article of manufacture of claim 15, wherein the method further comprises:

using data from a pre-scan of the volume of patient anatomy to determine positions of the one or more saturation areas proximate to the target volume of the patient anatomy; and acquiring the two or more slices of the image having the one or more saturation areas at the determined positions.

17. The article of manufacture of claim 16, wherein the method further comprises:

determining the positions of the one or more saturation areas by detecting a boundary of the target volume of the patient anatomy in the pre-scan; and positioning the one or more saturation areas at the edge of the detected boundary of the target volume of the patient anatomy.

* * * * *